(12) United States Patent
Soliman et al.

(10) Patent No.: US 7,886,739 B2
(45) Date of Patent: Feb. 15, 2011

(54) SYSTEM AND METHOD FOR CIRCUIT COMPLIANCE COMPENSATED VOLUME CONTROL IN A PATIENT RESPIRATORY VENTILATOR

(75) Inventors: Ihab S. Soliman, Laguna Niguel, CA (US); Steven Duquette, Laguna Niguel, CA (US)

(73) Assignee: Carefusion 207, Inc., San Diego, CA (US)

( * ) Notice: Subject to any disclaimer, the term of this patent is extended or adjusted under 35 U.S.C. 154(b) by 1402 days.

(21) Appl. No.: 11/247,568

(22) Filed: Oct. 11, 2005

(65) Prior Publication Data

US 2007/0089738 A1      Apr. 26, 2007

(51) Int. Cl.
| | |
|---|---|
| A61M 15/00 | (2006.01) |
| A61M 16/00 | (2006.01) |
| G06F 19/00 | (2006.01) |
| G06F 15/00 | (2006.01) |
| G06F 17/00 | (2006.01) |
| G06F 7/00 | (2006.01) |
| G06D 9/00 | (2006.01) |
| G05D 16/00 | (2006.01) |
| G04F 5/00 | (2006.01) |
| B67B 7/00 | (2006.01) |
| B67D 7/00 | (2010.01) |
| B67D 1/00 | (2010.01) |

(52) U.S. Cl. .................. 128/204.21; 128/200.24; 128/203.12; 128/203.13; 128/204.18; 128/204.22; 128/204.23; 128/204.24; 128/204.25; 128/204.26; 702/1; 702/45; 702/50; 702/55; 702/127; 702/138; 700/90; 700/213; 700/231; 700/240; 700/244; 700/281; 700/282; 700/301; 700/305; 222/1; 222/2; 222/25; 222/52

(58) Field of Classification Search ............ 128/200.24, 128/203.12, 203.13, 204.18, 204.21, 204.22, 128/204.23, 204.24, 204.25, 204.26; 702/1, 702/45, 50, 55, 127, 138; 700/90, 213, 231, 700/240, 244, 281, 282, 301, 305; 222/1, 222/3, 52, 25

See application file for complete search history.

(56) References Cited

U.S. PATENT DOCUMENTS 5,881,717 A     3/1999  Isaza
6,305,374 B1 *  10/2001 Zdrojkowski et al. .. 128/204.21

* cited by examiner

*Primary Examiner*—Patricia M Bianco
*Assistant Examiner*—Nihir Patel
(74) *Attorney, Agent, or Firm*—Baker & Hostetler LLP

(57) ABSTRACT

A circuit compliance compensated volume control system in a patient respiratory ventilation system and method, including: a circuit compliance estimator, to provide a relationship between a circuit volume and a differential pressure between a circuit pressure and a positive end-expiratory pressure (PEEP) of the respiratory circuit, a circuit volume estimator, operative to provide an estimated circuit volume based on the relationship between the circuit volume and the differential pressure, a patient volume observer, operative to provide an estimated patient volume by subtracting the estimated circuit volume from a measured machine delivered net volume, and a volume delivery controller, operative to update the machine delivered net volume based on the estimated patient volume and a set tidal volume.

51 Claims, 4 Drawing Sheets

SYSTEM AND METHOD FOR CIRCUIT COMPLIANCE COMPENSATED VOLUME CONTROL IN A PATIENT RESPIRATORY VENTILATOR

CROSS-REFERENCE TO RELATED APPLICATIONS

Not Applicable

STATEMENT RE: FEDERALLY SPONSORED RESEARCH/DEVELOPMENT

Not Applicable

BACKGROUND

The present invention relates in general to a system and a method for circuit compliance compensated volume control in a patient respiratory ventilation system, and more particularly, to a respiratory ventilation system suitable for use in all ages and sizes of patients by effectively and accurately estimating and compensating for the patient circuit compliance In order to deliver an accurate set tidal volume to a patient in a respiratory ventilation system, the patient circuit compliance has to be compensated. The compensation of patient circuit compliance is especially crucial for neonatal patients whose lung compliance can be as small as about one thirteenth of the circuit compliance. Without compensating the circuit compliance, inaccurate volume and inadequate flow will be delivered to the patient. Therefore, various designs and algorithms have been proposed to facilitate the patient circuit compliance compensation in the respiratory ventilation system. Currently, the settings or approaches in many of the circuit compliance compensation designs or algorithms actually impact the ability of exhaling delivered tidal volume for the patient and consequently causing gas trapping and auto PEEP. Therefore, most of the ventilators available in the market do not allow the circuit compliance compensation designs applied to neonatal patients due to the stringent precision requirement on volume delivery. The burden of achieving accurate volume delivery is thus left for the clinician.

Currently, two algorithms that directly add an estimate of patient circuit volume to a set tidal volume are commonly used. In one of the commonly used algorithms, an estimate of patient circuit volume is directly added to a set tidal volume by extending the inspiratory time with a specific peak flow. The patient circuit volume is computed using the peak airway pressure (measured by an expiratory pressure transducer) and an estimate of the patient circuit compliance. As understood, the extension of inspiratory time often impacts the ability of the patient to exhale the delivered tidal volume; and consequently, results in gas trapping and auto PEEP. Such adverse effects are much more significant for young pediatric or neonatal patients whose lung compliance is comparative to or as small as only $\frac{1}{13}$ of the patient circuit compliance. Therefore, patient circuit compliance compensation based on the first algorithm is not suitable for those patients with small lung compliance. In addition, such algorithm is not responsive when changes in airway resistance and/or lung compliance occur.

In the second approach, an estimate of patient circuit volume is added to set tidal volume by increasing the preset peak inspiratory flow, which ultimately causes the increment of the average peak airway pressure. The patient circuit volume is computed using the average peak airway pressure of previous (four) mandatory/machine breaths and an estimate of the patient circuit compliance. The patient circuit volume is thus continuously elevated breath after breath. Due to positive feedback of average peak airway pressure, the second algorithm can establish a runaway (not converge) condition on neonatal patient size where the ratio of circuit compliance to patient (lung) compliance is as high as 13:1. Moreover, this algorithm is not robust in cases where airway resistance is high due to effects such as gas compression which occurs as a result of positive feedback of peak airway pressure. Therefore, this algorithm is only effective on adults and some pediatrics patient sizes, and it is not responsive when changes in airway resistance and/lung compliance occur either.

It is therefore a substantial need to develop a system and a method operative to provide circuit compensated volume control in a patient respiratory ventilation system without any of the above adverse effect and clinically acceptable for all patient sizes.

BRIEF SUMMARY

A system and a method for circuit compliance compensated volume control in a patient respiratory ventilation system clinically acceptable for patients at all sizes and ages are provided. The system and method as provided allow the patient to receive an accurate inspiratory flow while maintaining a constant ratio of inspiratory time versus expiratory time (I:E ratio) throughout volume delivery. As the constant I:E ratio is maintained, gas trapping and auto PEEP is prevented. The existing on-board sensors are used for estimating the volume required for compensating the patient circuit compliance and determining the accurate inspiratory flow, such that no additional device is required for implementing the system and method as provided. The operation of the system and the method is designed based on the governing physics of the patient and the ventilation system, such that the leakage through the expiratory limb during volume delivery by the ventilator and access volume delivery due to valve dynamic of the ventilator are accounted for. Therefore, the system and method are robust against changes in airway resistance and patient compliance.

The system for circuit compliance compensated volume control in a patient respiratory ventilation system can be divided into three main subsystems, including a flow regulated feedback servo control loop, a volume delivery controller, and a patient volume observer. In the flow regulated feedback servo control loop, an estimate of patient volume or a measured patient volume is used for feedback control, such that delivery of the set tidal volume to the patient can be achieved. The inspiratory flow is modulated based on volume error between the set tidal volume and the estimated patient volume. Thereby, a constant inspiratory time and a constant I:E ratio can be maintained. In the volume delivery control, the feedback volume error is normalized to a volume error percentage, and the feedback volume error is weighed by a gain which is dynamically determined based on the volume error percentage. Thereby, the desired tidal volume can be obtained with the minimized controller effort. The patient volume observer is operative to estimate the patient volume based on the estimated circuit volume and the measured machine delivered net volume, while the volume affected by leakages of expiratory limb and valve dynamics is synchronously captured with true patient breath.

The method for circuit compliance compensated volume control includes the steps of estimating a patient volume based on an estimated circuit volume and a measured machined delivered net volume; regulating the machine delivered net volume based on a feedback of the estimated patient volume; and modulating the inspiratory flow. The estimated circuit volume is obtained by a relationship between the circuit volume and the circuit pressure estimated based on the circuit compliance. The machine delivered net volume is regulated with a dynamic gain scheduling. More specifically, a gain is dynamically adjusted upon a normalized volume error defined as the ratio of volume differential between the set tidal volume and the estimated patient volume to the set tidal volume. Thereby, the desired inspiratory flow can be modulated and the patient volume can be estimated while a constant inspiratory time and I:E ratio can be maintained.

A ventilation system that incorporating the above volume control system is also provided. The ventilation system includes a ventilator for supplying inspiratory gas to the patient and receiving the expiratory gas exhaled from the patient. The system further comprises a patient circuit, preferably a Y-circuit for delivering the inspiratory and expiratory gas to and from the patient, respectively. Sensors and transducers are provided to measure the inspiratory and expiratory flows, the Y-circuit pressure and the PEEP. By the reading of existing flow sensors and pressure transducers and computation of the readings, the circuit compliance compensated volume control system is operative estimate the circuit volume and the patient volume based on the measured results and the estimated patient volume, so as to provide a circuit compliance volume compensation factor to regulate the machine delivered net volume, and thus delivered to modulate the insipratory flow, so as to delivery a desired tidal volume to the patient.

BRIEF DESCRIPTION OF THE DRAWINGS

These and other features and advantages of the various embodiments disclosed herein will be better understood with respect to the following description and drawings, in which like numbers refer to like parts throughout, and in which.

DETAILED DESCRIPTION

Figure 1:
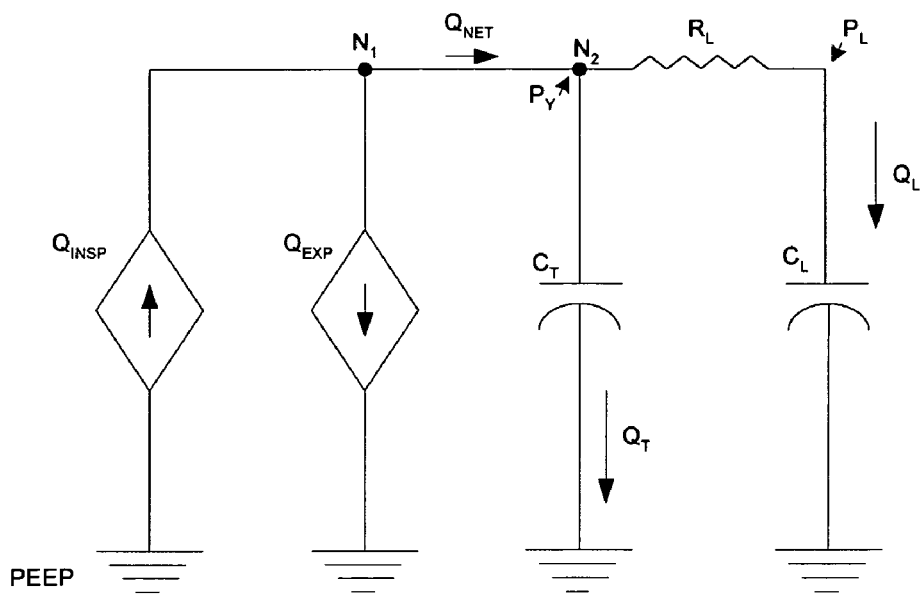
FIG. 1 illustrates a respiratory circuit diagram of a patient who is receiving machine ventilation.

In an electric circuit, the electric current I flows from a high potential level to a low potential level. When the electric current I flows through a passive circuit element such as a resistor, an inductor, a capacitor or a load, a voltage drop $\Delta V$ is created across such element. When two or more of the passive circuit elements of the electric circuit are connected to each other in parallel, the total electric current is split into two smaller currents distributed flowing through the respective elements. The magnitudes of the currents depend on the characteristic values, such as the resistance, the conductance, and the capacitance of the elements. In a patient respiratory circuit, the gas flow Q circulates from a high pressure level to a low pressure level in a way similar to the electric current I, and the gas flow Q through a circuit element such as an airway resistance causes a pressure drop $\Delta P$ similar to the voltage drop $\Delta V$ in the electric circuit. FIG. 1 illustrates a circuit diagram of a patient respiratory circuit. As shown, the patient respiratory circuit typically comprises a patient circuit for circulating gas between a ventilator and a patient. The ventilator is operative to provide an inspiratory gas flow $Q_{INSP}$ and receive an expiratory gas flow $Q_{EXP}$ to and from the patient through the patient circuit, respectively. Ideally, the flow differential between the inspiratory flow $Q_{INSP}$ and the expiratory flow $Q_{EXP}$, that is, the net flow $Q_{NET}$, is all to be delivered to the patient, so as to provide the tidal volume required thereby. However, in real practice, the volume loss within the patient circuit is inevitable due to the distensibility at least partially attributed to the circuit compliance $C_T$ thereof. The circuit compliance $C_T$ is in parallel flow communication with the lung compliance $C_L$ and behaves similarly to a capacitor in an electric circuit.

Without the circuit compliance compensation, the machine delivered net volume $V_{NET}$ integrated by the net gas $Q_{NET}$ flow $Q_{NET}$ is equivalent to the tidal volume delivered to the patient. However, as discussed above, as a portion of the net gas flow $Q_{NET}$ is offset by the circuit compliance $C_T$n, the volume actually delivered to the patient's lung is actually smaller than the required tidal volume. Further, as the circuit compliance $C_T$ is defined as a ratio of the volume offset by the patient circuit to the pressure across the patient circuit. The offset volume is proportional to the circuit compliance $C_T$. Therefore, when the circuit compliance $C_T$ is much larger than the lung compliance $C_L$, a majority of the net flow $Q_{NET}$ will be distributed to the patient circuit instead of being supplied to the patient's lung.

In this embodiment, the patient circuit is connected to a ground pressure level PEEP. Therefore, the pressure across the patient circuit is thus the pressure differential between the pressure measured at a patient piece of the patient circuit $P_Y$ and PEEP. In this embodiment, an airway resistance $R_L$ exists in the patient's airway, such that the pressure applied to the patient's lung will be reduced by a factor of $Q_L^2 R_L$. The pressure at the patient circuit $P_Y$ and the lung pressure $P_L$ can be expressed by the following equation:

$$P_Y = P_L + Q_L^2 R_L \tag{1}$$

By definition, the circuit compliance $C_T$ and the lung compliance $C_L$ can be expressed as:

$$C_L = \frac{V_{TID}}{P_L - PEEP}; \text{ and} \tag{2}$$

$$C_T = \frac{V_{CC}}{P_Y - PEEP}, \tag{3}$$

where $V_{TID}$ is equivalent to $V_L$, which is the actual gas volume delivered to the lung of the patient, and $V_{CC}$ is the gas volume offset by the circuit compliance. The gas volumes $V_{TID}$ and $V_{CC}$ can be derived by integrating the gas flow $Q_T$ and $Q_L$ flowing through the patient circuit and the patient's lung L. Therefore, the sum of the gas volumes $V_{CC}$ and $V_L$ is equal to the machine delivered net volume $V_{NET}$ as expressed by Equation (4), which can be integrated from the net gas flow $Q_{NET}$.

$$V_{NET} = V_{CC} + V_{TID} \tag{4}$$

From Equations (3) and (4), an estimate of patient volume can be expressed as:

$$\hat{V}_{TID} = V_{NET} - V_{CC} = V_{NET} - C_T(P_Y - PEEP) \tag{5}$$

From Equations (1) and (2), $$P_Y - PEEP = \frac{V_{TID}}{C_L} + Q_L^2 R_L. \qquad (6)$$

From Equations (5) and (6), an estimate of the net volume that the ventilator needs to deliver is:

$$V_{NET} = V_{TID} + C_T(P_Y - PEEP) \text{ or} \qquad (7)$$

$$V_{NET} = V_{TID} + C_T\left(\frac{V_{TID}}{C_L} + Q_L^2 \cdot R_L\right); \text{ and therefore,}$$

$$\hat{V}_{NET} = \left(1 + \frac{C_T}{C_L}\right)V_{TID} + C_T \cdot Q_L^2 \cdot R_L.$$

From Equation (7), the machine delivered net volume $V_{NET}$ can be computed if the lung compliance $C_L$, the circuit compliance $C_T$, the airway resistance $R_L$, the desired patient flow $Q_L$, and the desired patient flow $V_{TID}$ are known. It will be appreciated that, as the volume parameters in Equation (7) are integrations of the corresponding gas flows, the pressure parameter $P_Y$ typically indicates the peak pressure at the patient circuit.

In Equation (7), since the lung compliance $C_L$ and the airway resistance $R_L$ can vary with time or condition, it would be very difficult to accurately determine the appropriate machine delivered volume as desired on a real-time basis to achieve a desired patient tidal volume. This appears to be the major reason that the conventional circuit compliance compensation design is only applicable to the patients having specific sizes of lungs. Therefore, as provided in this embodiment, the system and method for circuit compliance compensated volume control estimate the patient circuit volume and a patient tidal volume using the existing sensors in the ventilator. The actual inspiratory gas flow $Q_{INSP}$ and the expiratory gas flow $Q_{EXP}$ are measured by the existing sensors of the ventilator, and the machine delivered net flow $Q_{NET}$ can be derived from the difference thereof. In such manner, various volume variables can be obtained based on the true inhalation and exhalation of the patient.

By definition, the positive end expiratory pressure PEEP is the pressure $P_Y$ measured at the end of the expiratory phase. Therefore, before the patient is receiving the machine ventilation, the ground pressure level of the patient circuit is zero or other preset values. The circuit compliance $C_T$ can be predetermined by supplying known volumes to the patient circuit and measuring the responsive circuit pressure at each specific circuit volume. The circuit compliance $C_T$ for a specific patient circuit can thus be expressed by an empirical relationship between the circuit volume $V_{CC}$ and the circuit pressure $\Delta P_Y(=P_Y)$. When the patient circuit is applied to circulating gas between the ventilator and the patient as shown in FIG. 1, one can thus derive the circuit volume $V_{CC}$ by providing the circuit pressure $\Delta P_Y(P_Y-PEEP)$ to the circuit compliance relationship. In this embodiment, the circuit pressure $P_Y$ is defined as the pressure measured at the expiratory limb of the patient circuit during the inspiratory phase, that is, $P_Y=P_{EXP}$ during I-phase; or $P_Y$ is the average pressure between $P_{EXP}$ and the pressure measured at the inspiratory limb of the patient circuit during the expiratory phase $P_{INSP}$, that is, $P_Y=(P_{INSP}+P_{EXP})/2$ during E-phase.

Figure 2:
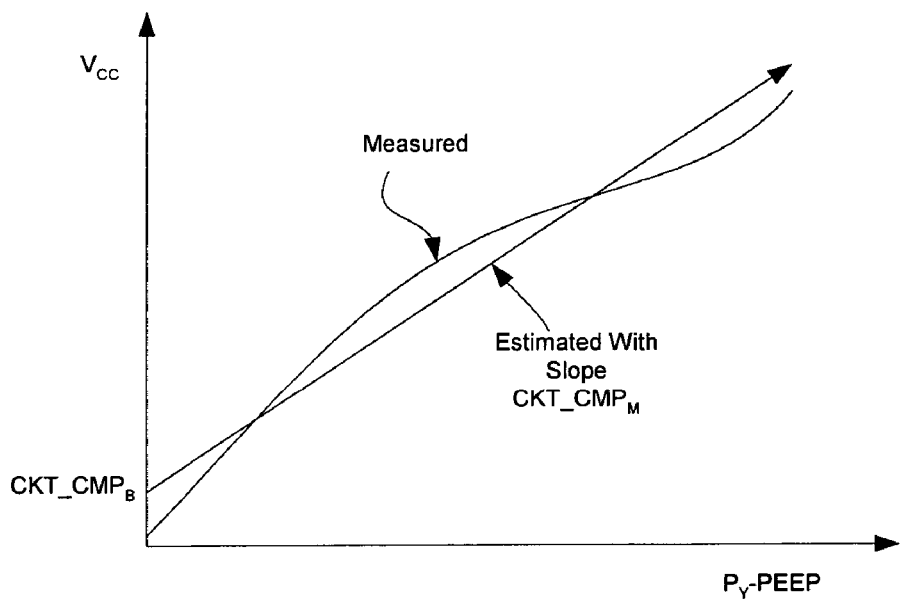
FIG. 2 shows a graph of circuit compliance obtained from empirical data and an estimated circuit compliance approximated from the empirical data.

FIG. 2 shows the relationship between the circuit volume $V_{CC}$ and the pressure differential $\Delta P_Y$ obtained from empirical data. As shown, the empirical data show a nearly linear relationship between the circuit volume $V_{CC}$ and the differential circuit pressure $\Delta P_Y$. Therefore, a linear line with a slope $CKT\_CMP_{SLP}$ that reflects the circuit compliance $C_T$ can be drawn from the graph, and the circuit volume $V_{CC}$ can be presented by the equation as:

$$\hat{V}_{CC} = CKT\_CMP_{SLP} \cdot (P_Y - PEEP) + CKT\_CMP_{INT} \qquad (8)$$

where $CKT\_CMP_{INT}$ is the intercept with the $V_{CC}$ axis. It will be appreciated that, in addition to mathematical formula as provided in Equation (8), a lookup table in which the empirical data of the responsive circuit volumes for various pressures can also be used to estimate the circuit volume $V_{CC}$. In addition, according to specific condition, a non-linear relationship between the circuit volume and the pressure may also be obtained and utilized for estimating the circuit volume.

When the circuit volume of the patient circuit is obtained, the tidal volume delivered to the patient can be estimated from Equation (4), that is, $$\hat{V}_{TID} = V_{NET} - \hat{V}_{CC} \qquad (9)$$

As mentioned above, the net volume delivered by the machine $V_{NET}$ can be derived by integrating the net flow delivered by the machine $Q_{NET}$, that is, the difference between the inspiratory and expiratory gas flows $Q_{INSP}$ and $Q_{EXP}$ as:

$$V_{NET} = \int_{Start\ of\ I\text{-}phase}^{Q_{NET}\ crosses\ 0} (Q_{INSP} - Q_{EXP}) dt. \qquad (10)$$

In this embodiment, the circuit volume $V_{CC}$ will not be updated until the differential gas flow, that is, the net gas flow $Q_{NET}(=Q_{INSP}-Q_{EXP})$, crosses zero; and therefore, the calculation or computation of the net machine delivered volume $V_{NET}$ is integrated over the differential gas flow $Q_{NET}$ from the start of the inspiratory phase to the time when the net flow $Q_{NET}$ crosses 0. In the case that the net flow $Q_{NET}$ crosses 0 before the inspiratory phase is complete, the circuit volume $V_{CC}$ and the tidal volume $V_{TID}$ are estimated at the end of the inspiratory phase.

Figure 3:
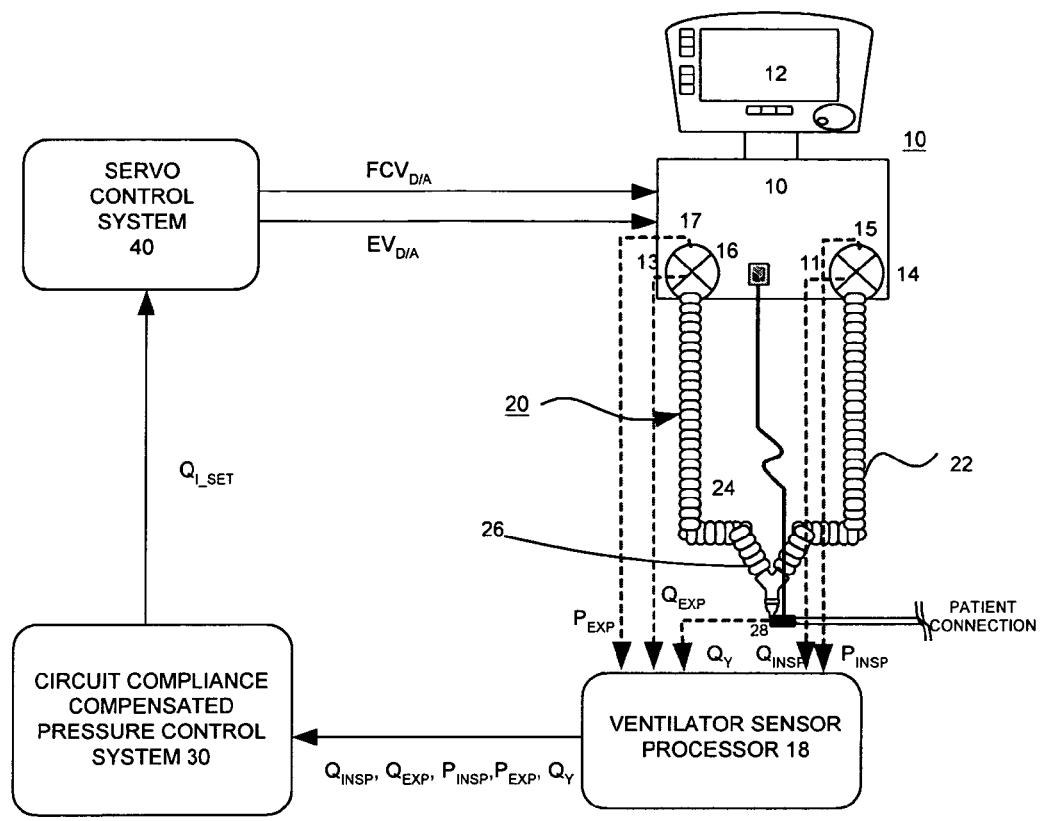
FIG. 3 illustrates a block diagram showing a ventilation system that incorporates a system for circuit compliance compensated volume control.

FIG. 3 illustrates a patient respiratory ventilation circuit or system incorporating the system for circuit compliance compensated volume control as discussed above. As shown in FIG. 3, the ventilation system includes a ventilator 10, a patient circuit 20 for circulating the inspiratory gas and expiratory gas between the ventilator 10 and a patient, the system for circuit compliance compensated volume control 30, and a servo control subsystem 40 for controlling operations of the ventilator 10. The ventilator 10 typically includes a user interface such as a monitor 12 for displaying various conditions and parameters of the patient and the ventilation system, and an input device (not shown) allowing the operator or user to input the required settings and parameters. The input device may include buttons or any adjusting devices built on the front panel or other devices including keyboard, mouse or remote controls allowing the user to input setup information to the ventilator 10. Alternatively, the monitor 12 may be in the form of a touch screen in which both the display and input device are integrated. Based on the input data or information, the processor is operative to control the ventilator 10 for performing the desired operations. The ventilator 10 further includes an inspiratory port 14 and an expiratory port 16 through which the inspiratory gas to the expiratory gas are supplied and received to and from the patient through the patient circuit 20, respectively. An inhalation flow control valve or orifice is typically installed at the inspiratory port 14 for controlling the inspiratory flow $Q_{INSP}$, and an exhalation valve is preferably installed at the expiratory port 16 for controlling the open/close condition of the expiratory port 16. In this embodiment, inspiratory and expiratory flow sensors 11 and 13 are installed at the inspiratory and expiratory ports 14 and 16 for measuring the inspiratory $Q_{INSP}$ and expiratory flow $Q_{EXP}$, respectively. In addition, an inspiratory pressure transducer 15 and an expiratory pressure transducer 17 may also be installed to measure the inspiratory and expiratory pressure $P_{INSP}$ and $P_{EXP}$, respectively.

As shown, the patient circuit 20, such as a Y circuit, is used to connect the ventilator 10 to the patient, so as to construct the respiratory circuit for circulating gas between the ventilator 10 and the patient. The Y circuit 20 includes an inspiratory limb 22 with one end connected to the inspiratory port 14 and an expiratory limb 24 with one end connected to the expiratory port 16 of the ventilator 10. The other ends of the inspiratory port 14 and the expiratory port 16 merge at one end of a patient piece 26, of which the other end is applied to the patient. Other accessories or component devices such as filters may also be installed in various part of the Y circuit 20. To directly measure the gas flow $Q_Y$ delivered to the patient, a flow sensor 28 is preferably installed at the patient piece 26. It will be appreciated that the inspiratory and expiratory flow sensors 11 and 13 and the inspiratory and expiratory pressure transducers 15 and 17 may also be installed on the inspiratory limb 22 and expiratory limb 24, respectively. Preferably, the measurable process variables, including the inspiratory flow $Q_{INSP}$, the expiratory flow $Q_{EXP}$, the inspiratory pressure $P_{INSP}$, the expiratory pressure $P_{EXP}$ and the PEEP are sampled by a predetermined frequency. For example, in one embodiment, these processes are sampled every 2 msec. The ventilator 10 may further comprise a sensor processor 18 operative to process the measured process parameters, including $Q_{INSP}$, $Q_{EXP}$, $P_{INSP}$, $P_{EXP}$ and other sensor readings before outputting to the circuit compliance compensated volume control system 30. The sensor processor 18 may includes an individual sensor in communication with the sensors 11, 13, 15, 17 and 28 and the circuit compliance compensated volume control system 30. Alternatively, the sensor processor 18 may be integrated into the above-mentioned processor of the ventilator 10 that control the operations of the ventilator 10.

Figure 4:
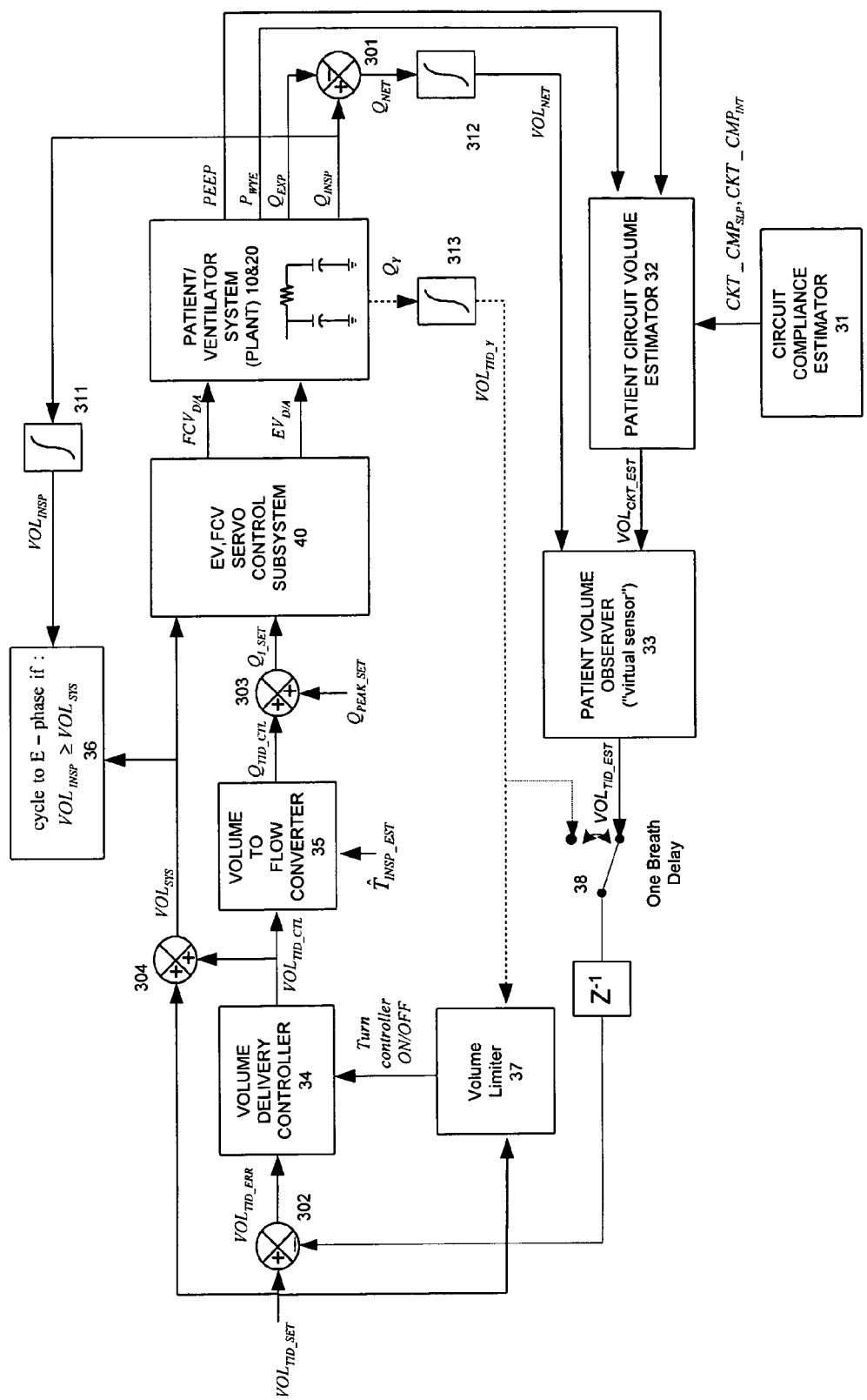
FIG. 4 snows a block diagram of the system for circuit compliance compensated volume control.

Referring to FIGS. 3 and 4, the system for circuit compliance compensated volume control 30 includes a circuit compliance estimator 31, a patient circuit volume estimator 32, a patient volume observer 33, a volume delivery controller 34, and a volume to flow converter 35. As discussed above, the circuit compliance $C_T$ of the patient circuit 20 can be estimated by measuring the pressure differential $\Delta P_Y$ at various given circuit volumes $V_{CC}$ before the patient is receiving the machine ventilation. In this embodiment, the circuit compliance estimator 31 is operative to estimate the circuit compliance $C_T$, such that the relationship between the circuit volume $V_{CC}$ and the pressure differential $\Delta P_Y$, including the slope CKT_CMP$_{SLP}$ and the intercept CKT_CMP$_{INT}$, can be also obtained. The slope CKT_CMP$_{SLP}$ and the intercept CKT_CMP$_{INT}$ of the circuit compliance estimator 31 are then output to the patient circuit volume estimator 32. The circuit volume estimator 32 is also connected to the ventilator 10 for receiving the Y circuit pressure $P_Y$ and the PEEP measured by the pressure transducer 17, such that the pressure differential $\Delta P_Y$ can be computed. Based on $\Delta P_Y$, the slope CKT_CMP$_{SLP}$ and the intercept CKT_CMP$_{INP}$, the patient circuit volume $V_{CC}$ can be estimated by Equation (8) and denoted as VOL$_{CKT\_EST}$ output to the patient volume observer 33. Again, it will be appreciated that, in addition to Equation (8) that mathematically expresses the relationship between the circuit volume $V_{CC}$ and the responsive pressure differential $\Delta P_Y$, the circuit compliance $C_T$ may also be in the form of a lookup table which provides the responsive pressure differentials for the circuit volumes based on empirical data.

The patient volume observer 33 is operative to receive the measured machine delivered net volume VOL$_{NET}$, that is, the machine delivered net volume derived by integrating the net flow $Q_{NET}$, and the estimated circuit volume VOL$_{CKT\_EST}$ obtained by the circuit volume estimator 32. By subtracting the estimated circuit volume VOL$_{CKT\_EST}$ from the measured machine delivered net volume VOL$_{NET}$, the patient volume, that is, the estimated tidal volume VOL$_{TID\_EST}$ actually delivered to the patient, is provided by the patient volume observer 33. Preferably, the estimated circuit volume VOL$_{CKT\_EST}$ and the estimated patient volume VOL$_{TID\_EST}$ are updated according to the timing when the net flow $Q_{NET}$ crosses zero instead of the timing when the machine breath cycles from inspiratory phase to expiratory phase. The update timing for the volume variables will be further discussed later.

In this embodiment, when a patient circuit disconnected is detected or when any type of circuit integrity alarm is activated, the volume variables will not be updated until the patient circuit is reconnected or the alarm is off. That is, the machine delivered net volume VOL$_{NET}$, the estimated patient volume VOL$_{TID\_EST}$ and the estimated circuit volume VOL$_{CKT\_EST}$ freeze at previously computed values as:

$$VOL_{NET_K} = VOL_{NET_{K-1}}$$

$$VOL_{TID\_EST_K} = VOL_{TID\_EST_{K-1}}; \text{ and}$$

$$VOL_{CKT\_EST_K} = VOL_{CKT\_EST_{K-1}} \quad (11)$$

where K is an index indicating the sampling number of the above volume variables. The sampling interval for these volume variables is determined based on factors such as the individual ventilator settings and the patient conditions.

When the flow sensor 28 is installed in the Y circuit 20, the patient flow $Q_Y$ can also be measured. The measured patient flow $Q_Y$ can be used to compute a measured patient volume VOL$_{TID\_Y}$ for facilitate volume limit of the circuit delivery controller 34, so as to prevent an excessive circuit compliance compensation volume factor VOL$_{TID\_CTL}$ from being generated. The measured patient volume VOL$_{TID\_Y}$ can also used to replace the estimated patient volume VOL$_{TID\_EST}$ for computing the circuit compliance compensation volume factor VOL$_{TID\_CTL}$. In addition, the inspiratory flow $Q_{INSP}$ may also be integrated to obtain the inspiratory volume VOL$_{INSP}$. The applications of the measured patient volume VOL$_{TID\_Y}$ and the inspiratory volume VOL$_{INSP}$ will be discussed in details later in this specification. Similarly to the volume variables expressed in Equation (11), computation of both the measured patient volume VOL$_{TID\_Y}$ are frozen whenever the patient circuit disconnect is detected or the alarm is activated as:

$$VOL_{TID\_Y_K} = VOL_{TID\_Y_{K-1}};$$

$$VOL_{INSP_K} = VOL_{INSP_{K-1}} \quad (11-1)$$

Preferably, at the start of every inspiratory phase, or whenever any user setup value of the ventilator 10 varies, the measured machine delivered net volume VOL$_{NET}$, the measured patient volume VOL$_{TID\_Y}$, and the inspiratory volume $VOL_{INSP}$ are reset to an initial value (0 in this embodiment) and updated from the initial value every sampling interval (2 msec in this embodiment) as:

$$VOL_{NET_{K-1}}=0, VOL_{NET_K}=(Q_{NET_K}/60)*0.002$$

$$VOL_{TID\_Y_{K-1}}=0, VOL_{TID\_Y_K}=(Q_{Y_K}/60)*0.002$$

$$VOL_{INSP_{K-1}}=0, VOL_{INSP_K}=(Q_{INSP_K}/60)*0.002 \quad (12)$$

During the inspiratory phase, the net flow $Q_{NET}$, the patient delivered flow $Q_Y$ and the inspiratory flow $Q_{INSP}$ are continuously monitored. When the inspiratory phase has started for at least a predetermined time (for example, $TIME_{INSP}>50$ msec) and the net flow $Q_{NET}$ cross zero (that is, when $Q_{NET_K}<0$ and $Q_{NET_{K-1}}>0$), a zero-crossing net flow $Q_{NET}$ is detected and flagged, while the machine delivered net volume $VOL_{NET}$, the measured patient volume $VOL_{TID\_Y}$, and the inspiratory volume $VOL_{INSP}$ are continuously updated as:

$$VOL_{NET_K}=VOL_{NET_{K-1}}+(Q_{NET_K}/60)*0.002,$$
$$VOL_{NET_K}=\max(VOL_{NET_K}, 0)$$

$$VOL_{TID\_Y_K}=VOL_{TID\_Y_{K-1}}+(Q_{Y_K}/60)*0.002,$$
$$VOL_{TID\_Y_K}=\max(VOL_{TID\_Y_K}, 0)$$

$$VOL_{INSP_K}=VOL_{INSP_{K-1}}+(Q_{INSP_K}/60)*0.002. \quad (13)$$

If the net flow $Q_{NET}$ has been detected to cross zero during the inspiratory phase, the estimated circuit volume $VOL_{CKT\_EST}$ and the estimated patient volume $VOL_{TID\_EST}$ are updated at the start of the expiratory phase following the inspiratory phase as:

$$\hat{VOL}_{CKT\_EST_K}=CKT\_CMP_{SLP}\cdot(P_{Y_K}-PEEP_K)+CKT\_CMP_{INT}$$

$$\hat{VOL}_{TID\_EST_K}=VOL_{NET_K}-\hat{VOL}_{CKT\_EST_K}$$

$$\hat{VOL}_{TID\_EST_K}=\max(\hat{VOL}_{TID\_EST_K}, 0) \quad (14)$$

and the machine delivered net volume $VOL_{NET}$ and measured patient volume $VOL_{TID\_Y}$ are reset to the initial setup values and, again, updated from the initial values as:

$$VOL_{NET_{K-1}}=0, VOL_{NET_K}=(Q_{NET_K}/60)*0.002,$$
$$VOL_{NET_K}=\min(VOL_{NET_K}, 0)$$

$$VOL_{TID\_Y_K}=0, VOL_{TID\_Y_K}=(Q_{Y_K}/60)*0.002,$$
$$VOL_{TID\_Y_K}=\min(VOL_{TID\_Y_K}, 0) \quad (15)$$

Under the condition that the net flow $Q_{NET}$ does not cross zero during the inspiratory phase, the machine delivered net volume $VOL_{NET}$ and the measured patient volume $VOL_{TID\_Y}$ will not be reset at the start of the expiratory phase. That is, the machine delivered net volume $VOL_{NET}$ and the measured patient volume $VOL_{TID\_Y}$ are continuously updated during the expiratory phase as, $$VOL_{NET_K}=VOL_{NET_{K-1}}+(Q_{NET_K}/60)*0.002,$$
$$VOL_{NET_K}=\max(VOL_{NET_K}, 0)$$

$$VOL_{TID\_Y_K}=VOL_{TID\_Y_{K-1}}+(Q_{Y_K}/60)*0.002,$$
$$VOL_{TID\_Y_K}=\max(VOL_{TID\_Y_K}, 0)$$

$$VOL_{INSP_K}=VOL_{INSP_{K-1}}+(Q_{INSP_K}/60)*0.002. \quad (16)$$

When the zero-crossing net flow $Q_{NET}$ is detected within a predetermined period of time such as 100 msec after the machine has cycled to the expiratory phase (that is, when $TIME_{EXP}>100$ msec and $Q_{NET_{K-1}}>0$ and $Q_{NET_K}<0$); or alternatively, when the expiratory has lasted over the predetermined period of time such as 100 msec before the net flow zero-crossing $Q_{NET}$ is detected (that is, $TIME_{EXP}<100$ msec and $Q_{NET_K}>0$), the estimated circuit volume $VOL_{CKT\_EST}$ and the estimated patient volume $VOL_{TID\_EST}$ are updated as Equation (14), and the machine delivered net volume $VOL_{NET}$ and the measured patient volume $VOL_{TID\_Y}$ are reset to the initial setup values and updated therefrom as:

$$VOL_{NET_{K-1}}=0, VOL_{NET_K}=(Q_{NET_K}/60)*0.002,$$
$$VOL_{NET_K}=\min(VOL_{NET_K}, 0)$$

$$VOL_{TID\_Y_K}=0, VOL_{TID\_Y_K}=(Q_{Y_K}/60)*0.002,$$
$$VOL_{TID\_Y_K}=\min(VOL_{TID\_Y_K}, 0) \quad (17)$$

In this embodiment, the measured machine delivered net volume $VOL_{NET}$ and the measured patient volume $VOL_{TID\_Y}$ are reset according to the timing of net flow zero-crossing $Q_{NET}$ instead of the phase of the machine breath phase. This allows calculations of the estimated circuit volume $VOL_{CKT\_EST}$ and the estimated patient volume $VOL_{TID\_EST}$ to be synchronized with true patient inhalation and exhalation. Thereby, a more accurately real patient volume can be computed. The estimated patient volume $VOL_{TID\_EST}$ is thus updated according to the timing of the net flow zero-crossing $Q_{NET}$, such that all the machine delivered net volume $VOL_{NET}$ can be accounted for when the patient breath and the machine breath are out of phase, that is, when the net flow $Q_{NET}$ does not cross zero at the time the machine breath is cycling to the expiratory phase.

At the beginning of every inspiratory phase, the estimate of the patient volume $VOL_{TID\_EST}$ is subtracted from a set tidal volume $VOL_{TID\_SET}$ to obtain a volume error $VOL_{TID\_ERR}$ reflecting the error of tidal volume between the setup value and the actual value as estimated. The volume error $VOL_{TID\_ERR}$ can thus be used to compute an estimated circuit compliance volume compensation factor $VOL_{TID\_CTL}$ by the volume delivery controller 34 to regulate the desired machine/system delivered net volume $VOL_{SYS}$, so to modulate the inspiratory flow $Q_{I\_SET}$ of the ventilator 10. In this embodiment, an initial output of the volume delivery circuit 34 is predetermined at the beginning of the computation, that is, the circuit compliance volume compensation factor $VOL_{TID\_CTL}$ is initialized as:

$$VOL_{TID\_CTL}=INI\_CKT\_VOL. \quad (18)$$

The circuit compliance volume compensation factor $VOL_{TID\_CTL}$ will be reset to the initial value $INI\_CKT\_VOL$ when the user settings of the ventilator 10 are changed. That is, any time when a new set of parameters is input to the system, the circuit compliance volume compensation factor $VOL_{TID\_CTL}$ will be reset to the initial value $INI\_CKT\_VOL$ and updated for every breath.

Figure 5:
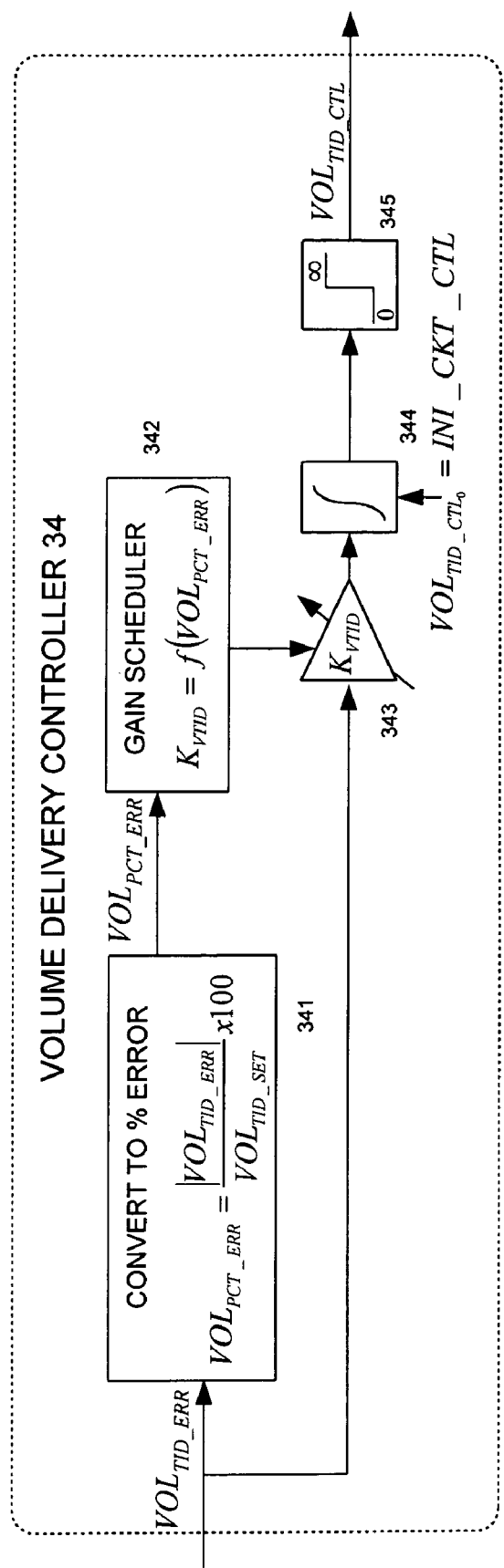
FIG. 5 illustrates a block diagram of a volume delivery controller of the system as shown in FIG. 4.

In the embodiment as shown in FIG. 5, the volume delivery controller 34 further comprises an error percentage converter 341, a gain scheduler 342, and a volume integrator 344 for generating the circuit compliance volume compensation volume factor $VOL_{TID\_CTL_K}$ for the current breath K. The error percentage converter 341 is used to compute a ratio of the feedback volume error $VOL_{TID\_ERR_K}$ to the set tidal volume $VOL_{TID\_SET_K}$ as:

$$VOL_{PCT\_ERR_K} = \frac{|VOL_{TID\_ERR_K}|}{VOL_{TID\_SET_K}} \times 100. \quad (19)$$

The error percentage $VOL_{PCT\_ERR_K}$ provides a useful indication of the ratio between the circuit compliance $C_T$ and the lung compliance $C_L$ of the patient. That is, when the error percentage $VOL_{PCT\_ERR_K}$ is larger, it indicates that a majority of the measured machine delivered net volume $VOL_{NET}$ is distributed to the patient circuit 20 instead of being supplied to the patient's lung. Under such circumstance, a larger amount of volume may be required to compensate for the circuit compliance $C_T$ in order to provide the correct machine delivered net volume $VOL_{SYS}$, so such sufficient volume can be delivered to the patient's lung. Therefore, the volume delivery controller 34 further comprises a gain scheduler 342 which receives the error percentage $VOL_{PCT\_ERR_K}$ and provides a gain $K_{VTID}$ according to the error percentage $VOL_{PCT\_ERR_K}$ for dynamically weighing the feedback volume error $VOL_{TID\_ERR_K}$, so as to according to the error percentage $VOL_{PCT\_ERR_K}$. A product of the gain $K_{VTID}$ and the volume error $VOL_{PCT\_ERR_K}$ is then obtained by a multiplier 343. The product of the gain $K_{VTID}$ and the volume error $VOL_{TID\_ERR_K}$, that is, the weighted volume error, is then added to the circuit compliance volume compensation factor $VOL_{TID\_CTL_{K-1}}$ computed in the previous breath in the integrator 344, and the circuit compliance compensated patient volume $VOL_{TID\_CTL_K}$ for the current breath can be estimated as:

$$VOL_{TID\_CTL_K} = K_{VTID} * VOL_{TID\_ERR_K} + VOL_{TID\_CTL_{K-1}} \quad (20)$$

The volume delivery controller 34 further comprises a volume restrictor 345 to prevent a negative circuit compliance volume compensation factor $VOL_{TID\_CTL_K}$ from being output. More specifically, the volume restrictor 345 restricts the output of the volume delivery controller 34 between a maximum value and zero as:

$$VOL_{TID\_CTL_K} = \max.(VOL_{TID\_CTL_K}, 0) \quad (21)$$

As discussed above, the measured patient volume $VOL_{TID\_Y}$ can be used as a volume limit to prevent the volume delivery controller 34 from generating an excessive volume factor to compensate for the circuit compliance. To this extent, the system for circuit compliance compensated pressure control 30 further comprises a volume limiter 37 operative to receive the measured patient volume $VOL_{TID\_Y}$ and compare the measured patient volume $VOL_{TID\_Y}$ to the set tidal volume $VOL_{TID\_SET}$. Before the measured patient volume $VOL_{TID\_Y}$ reaches a set tidal volume $VOL_{TID\_SET}$ preset by the user, that is, when $VOL_{TID\_Y} < VOL_{TID\_SET}$, the volume delivery controller 34 operates normally to generate the circuit compliance volume compensation factor $VOL_{TID_{CTL}}$ based on Equation (20). When the measured patient volume $VOL_{TID\_Y}$ reaches the set tidal volume $VOL_{TID\_SET}$, the volume error $VOL_{TID\_ERR}$ is set as zero:

$$VOL_{TID\_ERR} = 0 \quad (22)$$

and the output of the volume delivery controller 34, that is, the circuit compliance volume compensation factor $VOL_{TID\_CTL}$ is frozen at the value computed in the previous breath as:

$$VOL_{TID\_CTL_K} = VOL_{TID\_CTL_{K-1}} \quad (23)$$

Effectively, the volume limiter 37 is operative to switch on or activate operation of the volume delivery controller 34 when the measured patient volume $VOL_{TID\_Y}$ is smaller than the set tidal volume $VOL_{TID\_SET}$, and to switch off or inactivate operation of volume delivery controller as soon as the measured patient volume $VOL_{TID\_Y}$ is equal to or exceeds the set tidal volume $VOL_{TID\_SET}$.

Table I shows an exemplary gain $K_{VTID}$ set up according to the error percentage $VOL_{PCT\_ERR}$:

TABLE I

| $K_{VTID}$ | $VOL_{PCT-ERR}$ |
|---|---|
| 1 | 0 |
| 2 | 25% |
| 2.5 | 50% |
| 4 | 100% |
| 4 | 150% |

According to Table I, when the error percentage $VOL_{PCT\_ERR_K}$ is 100% and 150%, the gain $K_{VTID}$ is set at 4, such that four times of the feedback volume error $VOL_{TID\_ERR_K}$ is added to the previously estimated circuit compliance volume compensation factor $VOL_{TID\_CTL_{K-1}}$. When the error percentage $VOL_{PCT\_ERR}$ drops to 50%, 25% and 0, the gain $K_{VTID}$ is consequently reduced to 2.5, 2, and 1, respectively. The empirical data shows that gain $K_{VTID}$ varies with the error percentage $VOL_{PCT\_ERR}$ effectively reconciles the desired machine/system delivered net volume such that the desired tidal volume can be achieved within four breath cycles.

The output $VOL_{TID\_CTK_K}$ of the volume delivery controller 34 is then converted into the a circuit compliance flow compensation factor as $Q_{TID\_CTL_K}$ by the volume-to-flow converter 35, such that the inspiratory gas flow $Q_{INSP}$ can be updated to provide the accurate volume to the patient as computed above. To convert the volume factor $VOL_{TID\_CTL_K}$ into the flow factor $Q_{TID\_CTL_K}$, the inspiratory time $T_{INSP\_EST_K}$ is estimated first. As it is known that the set tidal volume $VOL_{TID\_SET_K}$ can be computed by the integration of a predetermined peak inspiratory flow $Q_{PEAK\_SET_K}$ time t throughout the inspiratory phase. Therefore, when the predetermined peak inspiratory flow $Q_{PEAK\_SET_K}$ and the set tidal volume $VOL_{TID\_SET_K}$ are known, the inspiratory tome $T_{INSP\_EST}$ can be estimated by such relationship. In this embodiment, the predetermined peak inspiratory flow $Q_{PEAK\_SET_K}$ is equal to a preset peak flow $Q_{PEAK\_USER_K}$ when a square waveform of the inspiratory flow is selected. In the case that a decelerating waveform is selected, the predetermined peak inspiratory flow $Q_{PEAK\_SET_K}$ is a function of the preset peak flow $Q_{PEAK\_USER_K}$ and the time t into the inspiratory phase. Therefore, dependent on the waveform as selected, the inspiratory time $T_{INSP\_EST}$ can be estimated as:

$$\hat{T}_{INSP\_EST_K} = \begin{cases} \dfrac{VOL_{TID\_SET_K}}{(Q_{PEAK\_USER}/60)}, & \text{square waveform} \\ \dfrac{(4/3) \cdot VOL_{TID\_SET_K}}{(Q_{PEAK\_USER}/60)}, & \text{decelerating waveform} \end{cases} \quad (24)$$

$$Q_{PEAK\_SET_K} = \begin{cases} Q_{PEAK\_USER}, & \text{square waveform} \\ f(Q_{PEAK\_USSER}, t), & \text{decelerating waveform} \end{cases} \quad (25)$$

where

The circuit compliance flow compensation factor $Q_{TID\_CTL_K}$ can thus be converted into the flow $Q_{TID\_CTL_K}$ as:

$$Q_{TID\_CTL_K} = 60 \cdot \left( \frac{VOL_{TID\_CTL_K}}{\hat{T}_{INSP\_EST_K}} \right). \tag{26}$$

Therefore, the required inspiratory flow $Q_{INSP\_SET_K}$ can be computed by:

$$Q_{I\_SET_K} = Q_{PEAK\_SET_K} + Q_{TID\_CTL_K} \tag{27}$$

while the overall commanded volume to be used by the servo-control subsystem 40 and to be used by breath control for cycling based on volume, that is, the desired machine/system delivered net volume $VOL_{SYS}$ is updated as:

$$VOL_{SYS_K} = VOL_{TID\_SET_K} + VOL_{TID\_CTL_K} \tag{28}$$

The inspiratory volume $VOL_{INSP}$ integrated from the measured inspiratory flow $Q_{INSP}$ can be used to determine the breath phase of the machine. As summarized by Equation (29), when the measured inspiratory volume $VOL_{INSP}$ is smaller than the updated or desired machine delivered net volume $VOL_{SYS}$, that is, the set tidal volume $VOL_{TID\_SET}$ compensated with the circuit compliance volume compensation factor $VOL_{TID\_CTL}$ ($VOL_{TID\_SET} + VOL_{TID\_CTL}$), the machine breath remains at the inspiratory phase. However, when the measured inspiratory volume $VOL_{INSP}$ is equal to or larger than the updated machine delivered net volume $VOL_{SYS}$, the machine breath enters or have entered the expiratory phase, respectively.

$$\text{phase} = \tag{29}$$
$$\begin{cases} \text{cycle to } E\text{-phase}, & VOL_{INSP\_K} \geq (VOL_{TID\_SET_K} + VOL_{TID\_CTL_K}) \\ \text{remain in } I\text{-phase}, & VOL_{INSP_K} < (VOL_{TID\_SET_K} + VOL_{TID\_CTL_K}) \end{cases}$$

As shown in FIG. 4, the system of circuit compliance compensated volume control 30 further comprises a plurality of adders/subtractors 301, 302, 303, and 304. As shown, the adder/subtractor 301 is operative to receive the inspiratory flow $Q_{INSP}$ and the expiratory flow $Q_{EXP}$, so as to calculate the net flow $Q_{NET}$ defined as the flow differential therebetween. The adder/subtractor 302 has two inputs to receive the set tidal volume $VOL_{TID\_SET}$ and the estimated patient volume $VOL_{TID\_EST}$ from the patient volume observer 32. Thereby, the difference between the set tidal volume $VOL_{TID\_SET}$ and the estimated patient volume $VOL_{TID\_EST}$, that is, the feedback volume error $VOL_{TID\_ERR_K}$ defined as the volume differential thereby can be derived and input to the volume delivery controller 34. The adder/subtractor 304 bypasses the volume-to-flow converter 35 to calculate the desired machine delivered net volume $VOL_{SYS}$ based on the set tidal volume $VOL_{TID\_SET}$ and the circuit compliance volume compensation factor $VOL_{TID\_CTL}$ computed by the volume delivery controller 34. The output of the adder/subtractor 304 is connected to the servo control subsystem 40 as well as a phase detector 36, which has another input connected to an integrator 311 for integrating the inspiratory flow $Q_{INSP}$ into the inspiratory volume $VOL_{INSP}$. By comparing the inspiratory volume $VOL_{INSP}$ and the output of the adder/subtractor 304, the phase detector 36 is operative to determine the current breath phase of the machine according to Equation (29). The adder/subtractor 303 has an input connected to the volume-to-flow converter 35, the other input for receiving the predetermined peak inspiratory flow $Q_{PEAK\_SET}$, and an output connected to the servo control sub-system 40. By the adder 303, the desired inspiratory flow $Q_{INSP\_SET}$ can be computed and input to the sub-system servo control system 40. In addition to the integrator 311, other integrators 312 and 313 can also be installed to compute the machine delivered volume $VOL_{NET}$ and the measured patient volume $VOL_{TID\_Y}$ when the patient flow $Q_Y$ is measured, respectively.

As discussed above, the measured machine delivered net volume $VOL_{NET}$ is input to the patient volume observer 33, and the measured tidal volume $VOL_{TID\_Y}$ can be used in a volume limiter 37 for controlling the maximum output of the volume delivery controller 34. In one embodiment, the measured tidal volume $VOL_{TID\_Y}$ can also be used to replace the estimated patient volume $VOL_{TID\_EST}$ for estimating the circuit compliance volume compensation factor $VOL_{TID\_CTL}$. To estimate the circuit compliance compensated volume based on the measured tidal volume $VOL_{TID\_Y}$, a switch 38 is inserted to selectively connect the adder/subtractor 302 to the integrator 313 or the patient volume observer 33. By simply operating the switch 38, the measured patient volume $VOL_{TID\_Y}$ or the estimated patient volume $VOL_{TID\_EST}$ can be selected as feedback for estimating the circuit compliance volume compensation factor $VOL_{TID\_CTL}$.

The above adders/subtractors 301-304 and integrators 311-313 may also be formed as individual in the system 30; or alternatively, they can also be integrated into the respective devices instead. For example, the integrators 311 and 312 may be integrated into the phase detector 36 and the patient volume observer 33, respectively, and the adder/subtractors 301, 302 and 303 may be integrated as a portion of the patient volume observer 33, the volume delivery controller 34, and the servo control sub-system 40, respectively. Alternatively, the adder/subtractor 303 may also be integrated at the output of the volume-to-flow converter 35, while the adder/subtractor 304 may also be integrated into the output of the volume delivery controller 34. In addition, the circuit compliance compensated volume control system 30 may be implemented by individual hardware or a processor integrated into the ventilator 10. The circuit compliance compensated volume control system 30 may also be implemented by a software executable by a personal or laptop computer connected to the ventilator or by the processor of the ventilator 10 directly.

As shown in FIGS. 3 and 4, the desired inspiratory flow $Q_{I\_SET}$ and the desired machine delivered volume $VOL_{SYS}$ are input to the servo control subsystem 40, which, according to the desired inspiratory flow $Q_{I\_SET}$, generate a flow-control valve command signal $FCV_{D/A}$ to control the orifice of the inspiratory port 14, so as to command the ventilator 10 to deliver the desired inspiratory flow $Q_{I\_SET}$. In addition to the flow-control valve command signal $FCV_{D/A}$, the servo control subsystem 40 is also operative to generate an exhalation valve command signal $EV_{D/A}$ to control opening or closing status of the exhalation port 16.

The above description is given by way of example, and not limitation. Given the above disclosure, one skilled in the art could devise variations that are within the scope and spirit of the invention disclosed herein, including various ways of implementing the circuit compliance compensated volume control systems. Further, the various features of the embodiments disclosed herein can be used alone, or in varying combinations with each other and are not intended to be limited to the specific combination described herein. Thus, the scope of the claims is not to be limited by the illustrated embodiments.

What is claimed is:

1. A circuit compliance compensated volume control system in a patient respiratory ventilation system, the volume control system comprising:
 a circuit compliance estimator, to provide a relationship between a circuit volume $V_{CC}$ and a differential pressure $\Delta P_Y$ between a circuit pressure $P_Y$ and a positive end-expiratory pressure PEEP of the respiratory circuit;
 a circuit volume estimator, operative to provide an estimated circuit volume $VOL_{CKT\_EST}$ based on the relationship between $V_{CC}$ and $\Delta P_Y$;
 a patient volume observer, operative to provide an estimated patient volume $VOL_{TID\_EST}$ by subtracting the estimated circuit volume $VOL_{CKT\_EST}$ from a measured machine delivered net volume $VOL_{NET}$; and
 a volume delivery controller, operative to update the machine delivered net volume $VOL_{NET}$ based on the estimated patient volume $VOL_{TID\_EST}$ and a set tidal volume $VOL_{TID\_SET}$,
 wherein the volume delivery controller further comprises:
  an error percentage converter for providing a volume error percentage $VOL_{PCT\_ERR}$ defined by a ratio of an absolute value of the volume error $VOL_{TID\_ERR}$ to the set tidal volume $VOL_{TID\_SET}$;
  a gain scheduler for determining a gain $K_{VTID}$ of the volume error as a function of the volume error percentage $VOL_{TID\_ERR}$; and
  a volume integrator for updating a circuit compliance volume compensation factor $VOL_{TID\_CTL}$ by adding a product of the gain $VOL_{VTID}$ and the volume error $VOL_{TID\_ERR}$ thereto,
  wherein the circuit compliance volume compensation factor $VOL_{TID\_CTL}$ is updated at the beginning of every inspiratory phase, and
  wherein the volume error $VOL_{TID\_ERR}$ is defined as the volume differential between the set tidal volume $VOL_{TID\_SET}$ and the estimated patient volume $VOL_{TID\_EST}$.

2. The system of claim 1, wherein:
 the relationship includes a linear relationship expressed as $V_{CC}=CKT\_CMP_{SLP}\cdot(P_Y-PEEP)+CKT\_CMP_{INT}$ in a $V_{CC}-\Delta P$ coordinate,
 $CKT\_CPM_{SLP}$ is a slope of the linear relationship, and
 $CKT\_CMP_{INT}$ is an intercept of the linear relationship and $\Delta P_Y$ axis.

3. The system of claim 1, wherein the circuit compliance estimator is operative to measure the responsive pressure differential $\Delta P_Y$ at various circuit volumes $V_{CC}$ before the patient is receiving the machine ventilation, so as to estimate the relationship.

4. The system of claim 1, wherein the measured machine delivered net volume $VOL_{NET}$ is derived by integration of a net flow $Q_{NET}$ defined as a differential flow between a measured inspiratory flow $Q_{INSP}$ and a measure expiratory flow $Q_{EXP}$.

5. The system of claim 4, further comprising an adder/subtractor for receiving the measured inspiratory and expiratory flows $Q_{INSP}$ and $Q_{EXP}$ to compute the net flow $Q_{NET}$.

6. The system of claim 5, further comprising an integrator for integrating the flow differential $Q_{NET}$ into the measured machine delivered net volume $VOL_{NET}$.

7. The system of claim 1, wherein the measured machine delivered volume $VOL_{NET}$ is updated and reset at the beginning of every inspiratory phase.

8. The system of claim 1, wherein when a measured differential flow $Q_{NET}$ crosses zero during an inspiratory phase, the estimated circuit volume $VOL_{CKT\_EST}$, the estimated patient volume $VOL_{TID\_EST}$ are updated and the measured machine delivered net volume $VOL_{NET}$ are reset at the start of the expiratory phase following the inspiratory phase.

9. The system of claim 8, wherein when the differential flow $Q_{NET}$ does not cross zero during the inspiratory phase, the estimated circuit volume and the estimated patient volume $VOL_{TID\_EST}$ are updated, and the measured machine delivered net volume $VOL_{NET}$ is reset when the differential flow $Q_{NET}$ crosses zero after the expiratory phase starts, or when the expiratory phase has started for a predetermined period of time before the differential flow $Q_{NET}$ has been detected to cross zero.

10. The system of claim 9, wherein the predetermined period is about 100 msec.

11. The system of claim 1, further comprising an adder/subtractor for computing the volume error $VOL_{TID\_ERR}$.

12. The system of claim 11, further comprising a volume-to-flow converter to convert the circuit compliance compensation factor $VOL_{TID\_CTL}$, into a circuit compliance flow compensation factor $Q_{TID\_CTL}$.

13. The system of claim 12, wherein:
 the circuit compliance flow compensation factor $Q_{TID\_CTL}$ is computed according to:

$$Q_{TID\_CTL} = 60 \cdot \left( \frac{VOL_{TID\_CTL}}{\hat{T}_{INSP\_EST}} \right), \text{ where } \hat{T}_{INSP\_EST}$$

is an estimated inspiratory time.

14. The system of claim 13, wherein the estimated inspiratory time $\hat{T}_{INSP\_ESP}$ is determined based on a predetermined peak inspiratory flow $Q_{PEAK\_SET}$ and the set tidal volume $VOL_{TID\_SET}$.

15. The system of claim 14, wherein the predetermined peak inspiratory flow $Q_{PEAK\_SET}$ equals to a preset peak inspiratory flow constant $Q_{PEAK\_USER}$ for a square waveform or a function of the preset peak inspiratory flow constant $Q_{PEAK\_USER}$ and time t into an inspiratory phase for a decelerating waveform.

16. The system of claim 15, wherein:

$$\hat{T}_{INSP\_EST} = \begin{cases} \dfrac{VOL_{TID\_SET}}{(Q_{PEAK\_USER}/60)} & \text{for square waveform} \\ \dfrac{(4/3) \cdot VOL_{TID\_SET}}{(Q_{PEAK\_USER}/60)} & \text{for decelerating waveform} \end{cases}.$$

17. The system of claim 12, further comprising an adder/subtractor to add the predetermined peak inspiratory flow $Q_{PEAK\_SET}$ with the circuit compliance flow compensation factor $Q_{TID\_CTL}$ into a required inspiratory flow $Q_{I\_SET}$.

18. The system of claim 1, wherein the volume delivery controller further comprises a volume restrictor to prevent the circuit compliance volume compensation factor $VOL_{TID\_CTL}$, that is lower than a minimum value from being output.

19. The system of claim 1, further comprising:
 a flow sensor operative to measure a patient flow $Q_Y$, and
 an integrator operative to provide a measured patient volume $VOL_{TID\_Y}$ by integrating the measured patient flow $Q_Y$.

20. The system of claim 19, further comprising a volume limiter operative to freeze computation of an output $VOL_{TID\_CTL}$ of the volume delivery controller when the measured patient volume $VOL_{TID\_Y}$ is larger than or equal to the set tidal volume $VOL_{TID\_SET}$.

21. The system of claim 19, wherein the measured patient volume $VOL_{TID\_Y}$ and $VOL_{NET}$ are reset at the beginning of every inspiratory phase.

22. The system of claim 19, wherein the measured patient volume $VOL_{TID\_Y}$ and the measured machine delivered net volume $VOL_{NET}$ are reset at the beginning of an expiratory phase when differential flow $Q_{NET}$ between a measured inspiratory flow $Q_{INSP}$ and a measured expiratory flow $Q_{EXP}$ crosses zero in an inspiratory phase followed by the expiratory phase.

23. The system of claim 22, wherein when the differential flow $Q_{NET}$ does not crosses zero during the inspiratory phase, the measured patient volume $VOL_{TID\_Y}$ and the measured machine delivered net volume $VOL_{NET}$ are reset at the time the differential flow $Q_{NET}$ crosses zero after the expiratory phase starts or when the expiratory phase has started for a predetermined period of time before the differential flow $Q_{NET}$ crosses zero.

24. The system of claim 1, wherein the circuit compliance volume compensation factor $VOL_{TID\_CTL}$ is reset to $INI\_CKT\_VOL$ whenever any user setting of the system is changed.

25. The system of claim 1, wherein the gain $K_{VTID}$ increases and decreases with the volume error percentage $VOL_{PCT\_ERR}$.

26. The system of claim 1, further comprising:
an adder/subtractor operative to add the circuit compliance volume compensation factor $VOL_{TID\_CTL}$ with the set tidal volume $VOL_{TID\_SET}$ into the desired machine delivered net volume $VOL_{SET\_CTL}$;
an integrator for integrating the measured inspiratory flow $Q_{INSP}$ into an actual inspiratory volume $VOL_{INSP}$; and
a phase detector for determining the current breathing phase by comparing the desired machine delivered net volume $VOL_{SET\_CTL}$ and the actual inspiratory volume $VOL_{INSP}$.

27. The system of claim 26, wherein the breathing cycles cycle from an inspiratory phase to an expiratory phase if $VOL_{INSP} \leq VOL_{SET\_CTL}$.

28. The system of claim 1, wherein the volume delivery controller comprises:
a gain scheduler for weighing a volume error $VOL_{TID\_ERR}$ according to a ratio of an absolute value of the volume error $VOL_{TID\_ERR}$ to the set tidal volume $VOL_{TID\_SET}$, wherein the volume error $VOL_{TID\_ERR}$ is defined as a volume differential between the measured patient volume $VOL_{TID\_EST}$ or the estimated patient volume $VOL_{TID\_EST}$ and the set tidal volume $VOL_{TID\_SET}$; and
a volume integrator to update the circuit compliance circuit volume compensation factor $VOL_{TID\_CTL}$ with the volume error $VOL_{TID\_ERR}$ weighed by the gain scheduler.

29. The system of claim 28, wherein the gain scheduler is operative to provide a gain that increases and decreases with the ratio of the volume error $VOL_{TID\_ERR}$ to the set tidal volume $VOL_{TID\_SET}$.

30. The system of claim 1, further comprising a volume-to-flow converter to convert the circuit compliance volume compensation factor $VOL_{TID\_CTL}$ into a circuit compliance volume flow compensation factor $Q_{TID\_CTL}$, so as to provide a desired inspiratory flow $Q_{I\_SET}$.

31. The system of claim 1, wherein the virtual sensor includes a Y flow sensor for measuring the patient volume $VOL_{TID\_Y}$ from the patient circuit.

32. The system of claim 31, wherein the measured machine delivered net volume $VOL_{NET}$ and the a measured patient volume $VOL_{TID\_Y}$ are reset at the beginning at every inspiratory phase.

33. The system of claim 31, wherein the measured machine delivered net volume $VOL_{NET}$ and the measured patient volume $VOL_{TID\_Y}$ are reset at the time an expiratory starts when a differential flow $Q_{NET}$ measured to compute the measured machine delivered net volume $VOL_{NET}$ crosses zero during an inspiratory phase followed by the expiratory phase.

34. The system of claim 33, wherein, when the differential flow $Q_{NET}$ does not cross zero during the inspiratory phase, the measured machine delivered net volume $VOL_{NET}$ and the measured patient volume $VOL_{TID\_Y}$ are reset when the differential flow $Q_{NET}$ crosses zero after the expiratory starts or when the expiratory phase has started for a predetermined period of time before the flow differential $Q_{NET}$ crosses zero.

35. A method for circuit compliance compensated volume control in a patient respiratory ventilation system, the method comprising:
a) estimating a patient volume $VOL_{TID\_EST}$ based on a machine delivered net volume and a circuit compliance of a patient circuit of the patient respiratory ventilation system, or measuring a patient volume $VOL_{TID\_Y}$ via a flow sensor located at a patient piece of the patient circuit; and
b) updating a circuit compliance volume compensation factor $VOL_{TID\_CTL}$ based on a set tidal volume $VOL_{TID\_SET}$ and a feedback volume error $VOL_{TID\_ERR}$, wherein the circuit compliance volume compensation factor $VOL_{TID\_CTL}$ has an initial setup value $INI\_CKT\_VOL_T$ and the feedback volume $VOL_{TID\_ERR}$ is defined as a volume differential between the patient volume $VOL_{TID\_EST}$ or $VOL_{TID\_Y}$ and the set tidal volume $VOL_{TID\_SET}$;
wherein step (b) further comprises:
b1) computing a volume error percentage $VOL_{PCT\_ERR}$ by dividing an absolute value of the volume error $VOL_{TID\_ERR}$ over the set tidal volume $VOL_{TID\_SET}$;
b2) determining a gain $K_{VTID}$ as a function of the volume error percentage $VOL_{PCT\_ERR}$; and
b3) updating the circuit compliance volume compensation factor $VOL_{TID\_CTL}$ by adding a product of the gain $K_{VTID}$ and the volume error $VOL_{TID\_ERR}$ thereto.

36. The method of claim 35, wherein the machine delivered net volume $VOL_{NET}$ and the measured patient volume $VOL_{TID\_Y}$ are reset and updated at the start of every inspiratory phase.

37. The method of claim 35, wherein, when the patient volume is estimated, step (a) further comprises:
a1) providing a machine delivered net flow $Q_{NET}$ by computing a flow differential of the inspiratory and expiratory flows $Q_{INSP}$ and $Q_{EXP}$; and
a2) integrating the machine delivery net flow $Q_{NET}$ into the machine delivered net volume $VOL_{NET}$.

38. The method of claim 37, wherein the estimated circuit volume $VOL_{CKT\_EST}$ the estimated patient volume $VOL_{TID\_EST}$ are updated, and the measured machine delivered net volume $VOL_{NET}$ and the measured patient volume $VOL_{TID\_Y}$ are reset at the start of an expiratory phase if the machine delivered net flow $Q_{NET}$ has been detected to cross zero during the inspiratory phase.

39. The method of claim 37, wherein, when the net flow $Q_{NET}$ does not cross zero during the inspiratory phase, the estimated circuit volume $VOL_{CKT\_EST}$ and the estimated patient volume $VOL_{TID\_EST}$ are updated, and the machine delivered net flow $VOL_{NET}$ and the measured patient volume $VOL_{TID\_Y}$ are reset at the earlier of when:
- the net flow $Q_{NET}$ crosses zero after the expiratory phase starts; and
- after the expiratory has started for over a predetermined time.

40. The method of claim 35, wherein step (a) further comprises:
- a3) providing a relationship between a patient circuit pressure $P_Y$ and a circuit volume $V_{CC}$ of the respiratory circuit;
- a2) providing an estimated circuit volume $VOL_{CKT\_EST}$ from a measured patient circuit pressure $P_Y$ and the relationship; and
- a3) providing the estimated patient volume $VOL_{TID\_EST}$ subtracting the estimated circuit volume $VOL_{CKT\_EST}$ from a machine delivered net volume $VOL_{NET}$.

41. The method of claim 35, further comprising converting the circuit compliance volume compensation factor $VOL_{TID\_CTL}$ into a circuit compliance flow compensation factor $Q_{TID\_CTL}$.

42. The method of claim 41, wherein:
the circuit compliance flow compensation factor $Q_{TID\_CTL}$ is computed according to:

$$Q_{TID\_CTL} = 60 \cdot \left( \frac{VOL_{TID\_CTL}}{\hat{T}_{INSP\_ESP}} \right), \text{ and } \hat{T}_{INSP\_ESP}$$

is an inspiratory time estimated based on the set tidal volume $VOL_{TID\_SET}$, a preset inspiratory peak flow $Q_{PEAK\_USER}$, and a pre-selected waveform.

43. The method of claim 41, further comprising providing an updated inspiratory flow $Q_{I\_SET}$ by adding the circuit compliance flow compensation factor flow $Q_{TID\_CTL}$, with a predetermined peak inspiratory flow $Q_{PEAK\_SET}$.

44. A circuit compliance compensated volume control method used for a patient receiving a machine ventilation through a patient circuit, the method comprising:
- providing a measured patient volume or an estimated patient volume by subtracting a circuit volume estimated based on a circuit compliance of the patient circuit from a measured machine delivered net volume;
- estimating a feedback volume error by computing a volume differential between the patient volume and a set tidal volume;
- computing a volume error percentage by dividing an absolute value of the volume error over the set tidal volume;
- weighing the feedback volume error by a gain defined by a function of the volume error percentage;
- presetting an initial value of a circuit compliance volume compensation factor; and
- updating the circuit compliance volume compensation factor based on the feedback volume error weighed by the gain.

45. The method of claim 44, further comprising a step of adjusting the gain when the error percentage varies.

46. The method of claim 44, wherein the gain is adjusted to zero when the feedback volume error is zero.

47. The method of claim 44, further comprising a step of resetting the measured machine delivered net volume at the beginning of every inspiratory phase.

48. The method of claim 44, further comprising resetting the measured machine delivered net volume at the beginning of an expiratory phase only when a measured machine delivered net flow crosses zero during an inspiratory phase followed by the expiratory phase.

49. The method of claim 48, further comprising, when the machined delivered net flow does not cross zero during the inspiratory phase, resetting the measured machine delivered net volume when:
- the machine delivered net flow crosses zero after the expiratory phase has started, or
- the expiratory phase has started over a predetermined period of time before the machine delivered net flow crosses zero.

50. The method of claim 44, further comprising converting the updated circuit compliance volume compensation factor into a circuit compliance flow compensation factor.

51. The method of claim 50, further comprising providing an updated inspiratory flow by adding the circuit compliance flow compensation factor with a predetermined peak inspiratory flow.

* * * * *